United States Patent
Finneran

(10) Patent No.: US 9,579,656 B2
(45) Date of Patent: Feb. 28, 2017

(54) ROTATION-LIMITING WELL PLATE ASSEMBLY

(71) Applicant: J.G. Finneran Associates, Inc., Vineland, NJ (US)

(72) Inventor: James G. Finneran, Vineland, NJ (US)

(73) Assignee: J. G. Finneran Associates, Inc., Vineland, NJ (US)

( * ) Notice: Subject to any disclaimer, the term of this patent is extended or adjusted under 35 U.S.C. 154(b) by 37 days.

(21) Appl. No.: 13/914,779

(22) Filed: Jun. 11, 2013

(65) Prior Publication Data
US 2014/0361022 A1 Dec. 11, 2014

(51) Int. Cl.
| | | |
|---|---|---|
| B65D 1/09 | (2006.01) | |
| B01L 9/06 | (2006.01) | |
| B65D 21/02 | (2006.01) | |
| B01L 3/00 | (2006.01) | |
| G01N 35/04 | (2006.01) | |

(52) U.S. Cl.
CPC ............ *B01L 9/06* (2013.01); *B01L 3/50855* (2013.01); *B01L 3/50825* (2013.01); *B01L 2200/025* (2013.01); *B01L 2300/04* (2013.01); *B01L 2300/042* (2013.01); *B01L 2300/0829* (2013.01); *B01L 2300/12* (2013.01); *G01N 2035/0405* (2013.01)

(58) Field of Classification Search
CPC .... B01L 9/06; B01L 3/50825; B01L 3/50855; B01L 2200/025; B01L 2300/04; B01L 2300/042; B01L 2300/0829; B01L 2300/12; G01N 2035/0405
USPC ................. 220/23.4, 23.83, 608, 23.89, 507
See application file for complete search history.

(56) References Cited

U.S. PATENT DOCUMENTS

| | | | |
|---|---|---|---|
| 5,108,386 A | 4/1992 | Finneran | |
| 5,454,481 A * | 10/1995 | Hsu .............................. | 220/608 |
| 5,750,075 A * | 5/1998 | Spike ........................... | 422/558 |
| 6,193,064 B1 | 2/2001 | Finneran | |
| 6,378,723 B1 * | 4/2002 | Casey .......................... | 220/608 |
| 6,939,513 B2 * | 9/2005 | Berray et al. ................ | 422/569 |
| 7,934,614 B2 | 5/2011 | Finneran | |
| 8,425,864 B2 * | 4/2013 | Haywood et al. ............ | 422/559 |
| 8,550,273 B2 * | 10/2013 | Levin et al. .................. | 220/1.5 |
| 2002/0033373 A1 * | 3/2002 | Robertson .................... | 211/59.2 |
| 2002/0164270 A1 * | 11/2002 | Hool et al. ..................... | 422/64 |
| 2003/0003023 A1 * | 1/2003 | Korpela ......................... | 422/99 |

(Continued)

*Primary Examiner* — J. Gregory Pickett
*Assistant Examiner* — Niki M Eloshway
(74) *Attorney, Agent, or Firm* — Stradley Ronon Stevens & Young, LLP

(57) ABSTRACT

A well plate assembly including a base plate and vials. The well plate assembly includes a base plate having a bottom, a perimeter having opposing edges, and a plurality of protrusions extending from the bottom spaced apart from each other to form a plurality of compartments sized and configured for releasably holding vials. Each of the compartments includes a convoluted anti-rotation feature recessed into the bottom. The vials each have a bottom wall, a first side wall segment extending upwardly from the bottom wall, and a second side wall segment extending from the first side wall segment to an open top. The first side wall segment includes at least one spline designed to mate with the convoluted anti-rotation feature to prevent rotation of the vials when a torque is applied, for example, during capping or de-capping operations.

16 Claims, 8 Drawing Sheets

(56) References Cited

U.S. PATENT DOCUMENTS

| | | |
|---|---|---|
| 2007/0104617 A1* | 5/2007 | Coulling et al. .............. 422/102 |
| 2007/0125677 A1* | 6/2007 | Oronsky et al. .............. 206/446 |
| 2009/0194546 A1* | 8/2009 | Lane .......................... 220/673 |
| 2010/0192813 A1* | 8/2010 | Fry et al. ................... 108/57.31 |
| 2011/0027914 A1* | 2/2011 | Bunce et al. ................ 436/518 |
| 2011/0204084 A1* | 8/2011 | Aronowitz ...................... 222/1 |
| 2011/0278254 A1* | 11/2011 | Petrosino ..................... 215/247 |
| 2011/0278304 A1* | 11/2011 | Annala et al. ................ 220/507 |
| 2012/0088714 A1* | 4/2012 | Kumar ..................... A61J 1/14 |
| | | 514/1.1 |
| 2012/0175368 A1* | 7/2012 | Dimson et al. .............. 220/241 |
| 2013/0109009 A1* | 5/2013 | Kessel ............................ 435/5 |
| 2015/0017078 A1* | 1/2015 | Fattinger et al. ............. 422/549 |

\* cited by examiner

ROTATION-LIMITING WELL PLATE ASSEMBLY

TECHNICAL FIELD

The present invention relates generally to well plate assemblies and, more particularly, well plate assemblies that combine vials and base plates having an anti-rotation feature used, for example, in the analytical chemistry and pharmaceutical markets.

BACKGROUND OF THE INVENTION

Analytical chemistry laboratories use a variety of different sized and shaped vials for different types of experimental assays, including, for example, sorbent assays, high-throughput screening assays, and combinatorial chemistry analysis. In those assays, there is a need to provide support for the vials used. Often, the support is necessary to maintain the vials in an upright position to facilitate chemical reactions, prevent assay fluids from escaping from the vials, enable movement of the vials without disturbing the assay, or meet other experimental considerations.

Various vial-holding devices, such as microplates or trays, have been used for assays performed in these laboratories. Multi-well sample plates, commonly referred to as microtitre plates or microplates, are commonly used to hold a large number of samples in a rectangular array of wells, 24 wells (4×6) or 96 wells (8×12) being typical examples, to be assayed using various techniques such as scintillation counting, luminometry, fluorimetry, kinetics, and the like. U.S. Pat. No. 6,193,064 titled "Multi-Tier Vial Plate" and issued to the inventor of the present application, James G. Finneran, teaches an exemplary vial plate for holding vials, which is incorporated into this document in its entirety for all purposes.

Many applications for the vials require a securely sealed cap. This requirement is especially true for laboratory sample vials and dispensers for injectable pharmaceuticals and medicinal agents. A common closure for vials involves a thread neck on the vial and a corresponding screw thread on the cap. Closure is attained and a seal obtained by twisting or rotating the cap onto the vial. Thus, screw thread closures require torque pressure to apply and remove the cap. Specially designed capping and de-capping devices can be used in conjunction with the multi-well sample plates or microplates in order to cap or de-cap a portion, a line, or all of the vials. For example, an automated opening and closing device for screw cap tubes is available through Hamilton Company USA, with offices in Reno, Nev.

Generally, vials used in analytical chemistry assays are made of plastic. Plastic vials may be preferred to provide for a desired amount of friction to prevent twisting of the vials, for example, during the capping and/or de-capping processes. Plastic vials are often suitable for use with aqueous solutions. For acid-based or solvent-based solutions, however, plastic can dissolve or degrade. To overcome the shortcomings of conventional plastic vials, glass vials may be preferred. Glass vials do not have a high coefficient of friction, however, and can easily move or twist in traditional microplate or well assemblies, especially when a torque is applied during the capping or de-capping process. Thus, a need remains for an improved assembly that allows for use of glass vials, which have an anti-rotation feature to prevent rotation of the vials when a torque is applied, for example, during capping or de-capping of the vials.

SUMMARY OF THE INVENTION

To meet this and other needs, and in view of its purposes, the present invention provides for a convoluted anti-rotation feature in the form of a recessed cutout in the bottom of the base plate, which corresponds to the cross section of the bottom and base portion of the vials. Once the vials are inserted into the base plate, the base of the vials mates with the convoluted anti-rotation feature recessed in or cut out of the bottom of the base plate. Therefore, if a torque is applied to the vials, for example, during capping or de-capping of the vials, the vials are fixed in position and unable to rotate.

According to one embodiment of the present invention, a well plate assembly includes a base plate and a plurality of vials. The base plate includes a bottom, a perimeter having opposing edges, and a plurality of protrusions extending from the bottom spaced apart from each other to form a plurality of compartments sized and configured for releasably holding the vials. Each of the compartments includes a convoluted anti-rotation feature recessed into the bottom where the convoluted anti-rotation feature has at least one lobe.

The protrusions may be substantially diamond-shaped, for example, in the form of a superellipse. The protrusions may be unconnected to and independent from one another. The bottom of the base plate may also include a plurality of openings which are centrally aligned with the plurality of compartments, for example, to allow fluid to escape the bottom of the base plate. The base plate may be formed in a unitary one-piece construction, for example, formed from aluminum or the like.

The vials each have a central axis, a bottom wall, a first side wall segment extending upwardly from the bottom wall, and a second side wall segment extending from the first side wall segment to an open top. The first side wall segment includes at least one spline radially extending about the central axis. The spline is designed to mate with the lobe of the convoluted anti-rotation feature, for example, forming a transition fit or an interference fit, to prevent rotation of the vials when a torque is applied.

The vials may be substantially cylindrical or tubular in shape. For example, the second side wall segment of the vial may be substantially circular in cross section. The vials may be formed of glass, for example, class A, type one borosilicate glass, so that the vials are suitable for use with aqueous, acid-based, and/or solvent-based solutions.

The base of the vial as well as the recess forming the convoluted anti-rotation feature may have a multi-lobed cross section, for example, such as a bi-lobed, trefoil, quatrefoil, cinquefoil, sisefoil, or the like. The bottom wall and the first side wall segment of the vials may correspond to and match the recess forming the convoluted anti-rotation feature and may include a multi-spline cross section, for example, such as bi-lobed, trefoil, quatrefoil, cinquefoil, sisefoil, or the like. In an exemplary embodiment, the bottom wall of the vial has a substantially quatrefoil cross section, the first side wall segment of the vial has a substantially quatrefoil cross section, and the recess of the base plate has a substantially quatrefoil cross section.

The vials may include an externally threaded neck in order to engage a threaded cap, for example. The vials may include a cap, such as crimp caps, snap caps, and threaded caps. The cap may include a propylene threaded closure with a polytetrafluoroethylene and silicon liner, for example.

The vial according to another embodiment of the present invention is suitable for use with a well plate. The well plate has a bottom, a perimeter having opposing edges, and a plurality of protrusions extending from the bottom spaced apart from each other to form a plurality of compartments sized and configured for releasably holding vials. The bottom of each compartment includes a convoluted anti-rotation feature recessed into the bottom of the well plate. The recess forming the convoluted anti-rotation feature includes at least one lobe. The vial includes a bottom wall, a first side wall segment extending upwardly from the bottom wall, a second side wall segment extending from the first side wall segment to an externally threaded neck portion having an open top, and a central axis. The first side wall segment includes splines radially extending about the central axis separated by recesses defining the bottom wall to have a multi-spline cross section. The splines are designed to mate with the respective lobes of the recessed anti-rotation feature to prevent rotation of the vial when a torque is applied. The multi-spline cross section may be bi-lobed, trefoil, quatrefoil, cinquefoil, sisefoil, or the like. In particular, the bottom wall may have a substantially quatrefoil cross section.

According to another embodiment of the present invention, a well plate assembly includes a base plate and a plurality of vials. The base plate includes a bottom, a perimeter having opposing edges, and an array of individual, substantially diamond-shaped protrusions extending from the bottom spaced apart from each other to form a plurality of compartments sized and configured for releasably holding tubular vials. Each of the compartments includes a convoluted anti-rotation feature recessed into the bottom. The recess forming the convoluted anti-rotation feature has a multi-lobed cross section having a plurality of lobes. The plurality of vials each have a central axis, a bottom wall, a first side wall segment extending upwardly from the bottom wall, and a second side wall segment extending from the first side wall segment to an externally threaded neck portion having an open top. The first side wall segment includes splines radially extending about the central axis separated by recesses and defining the bottom wall to have a multi-spline cross section. The bottom wall and the splines of the first side wall segment are designed to mate with the respective lobes of the recessed anti-rotation feature in the bottom of the base plate to prevent rotation of the vial when a torque is applied. The torque may be applied to the vials when a cap is applied (e.g., during capping) or when a cap is removed (e.g., during de-capping), for example.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The present invention provides for an improved well plate assembly that allows for use of glass vials in a base plate, which have an anti-rotation feature to prevent rotation of the vials. In particular, rotation of the vials may be minimized or eliminated when a torque is applied, for example, during capping or de-capping of the vials.

According to one embodiment, the present invention provides a well plate assembly including a base plate and a plurality of vials. The base plate includes a bottom, a perimeter having opposing edges, and a plurality of protrusions extending from the bottom spaced apart from each other to form a plurality of compartments sized and configured for releasably holding the vials. Each of the compartments includes a convoluted anti-rotation feature recessed into the bottom; the recesses forming the convoluted anti-rotation feature have at least one lobe. The vials each have a central axis, a bottom wall, a first side wall segment extending upwardly from the bottom wall, and a second side wall segment extending from the first side wall segment to an open top. The first side wall segment includes at least one spline radially extending about the central axis. The spline is designed to mate with the lobe of the recessed convoluted anti-rotation feature to prevent rotation of the vials when a torque is applied. The torque may be applied to the vials during a capping or de-capping operation, for example.

Figure 1:
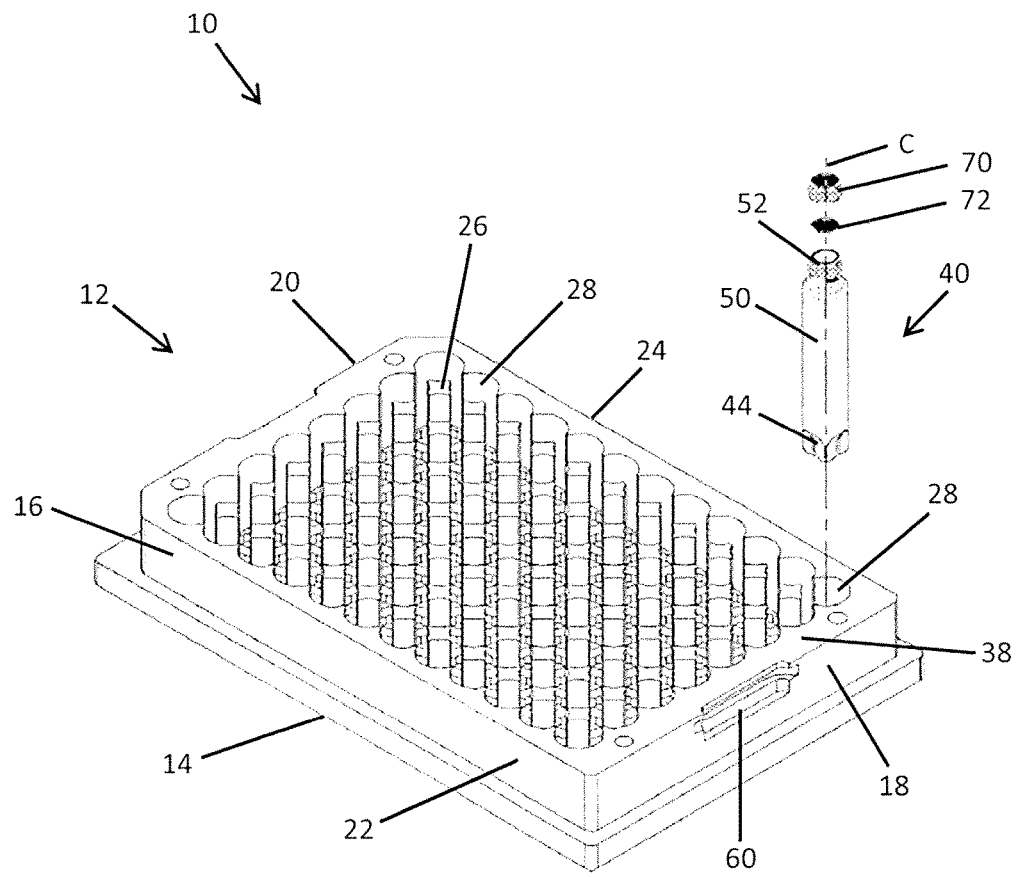
FIG. 1 shows a perspective view of the base plate and a vial according to one embodiment of the present invention.

Referring now to the drawing, in which like reference numbers refer to like elements throughout the various figures that comprise the drawing, FIG. 1 shows a perspective view of the well plate assembly 10 including a base plate 12 and a vial 40. Although only one vial 40 is depicted, it is to be understood that any suitable number of vials 40 may be included in the well plate assembly 10 sufficient to fill the base plate 12 or to meet the needs of a particular application. For example, for the base plate 12 depicted with an array of eight by twelve (8×12) or ninety-six (96) compartments 28, this base plate 12 may hold up to ninety-six (96) vials 40. In the case of a base plate 12 with an array of four by six (4×6) or twenty-four (24) total compartments 28, the base plate 12 may hold up to twenty-four (24) vials 40.

Vials

Figure 2:
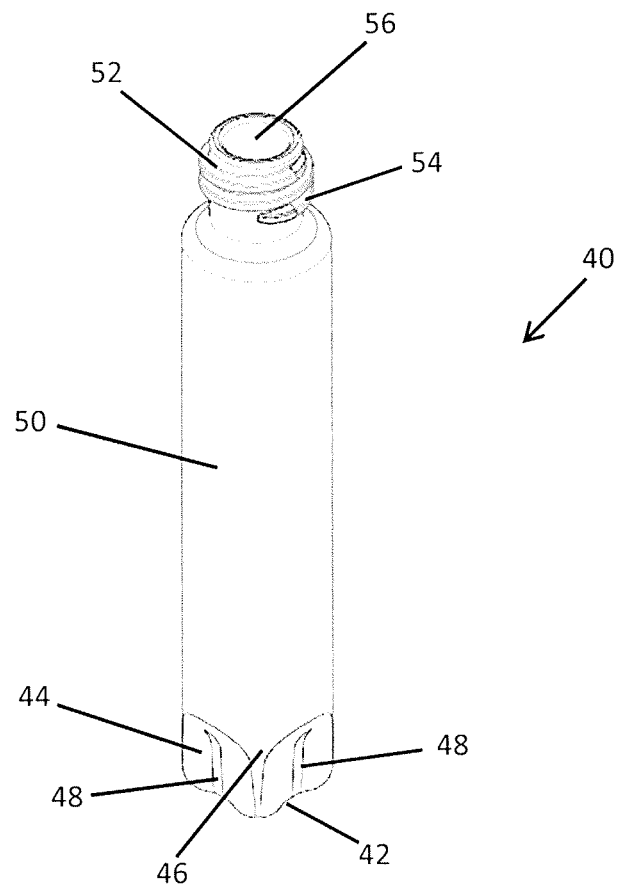
FIG. 2 shows a close-up perspective view of the vial shown in FIG. 1.
Figure 5:
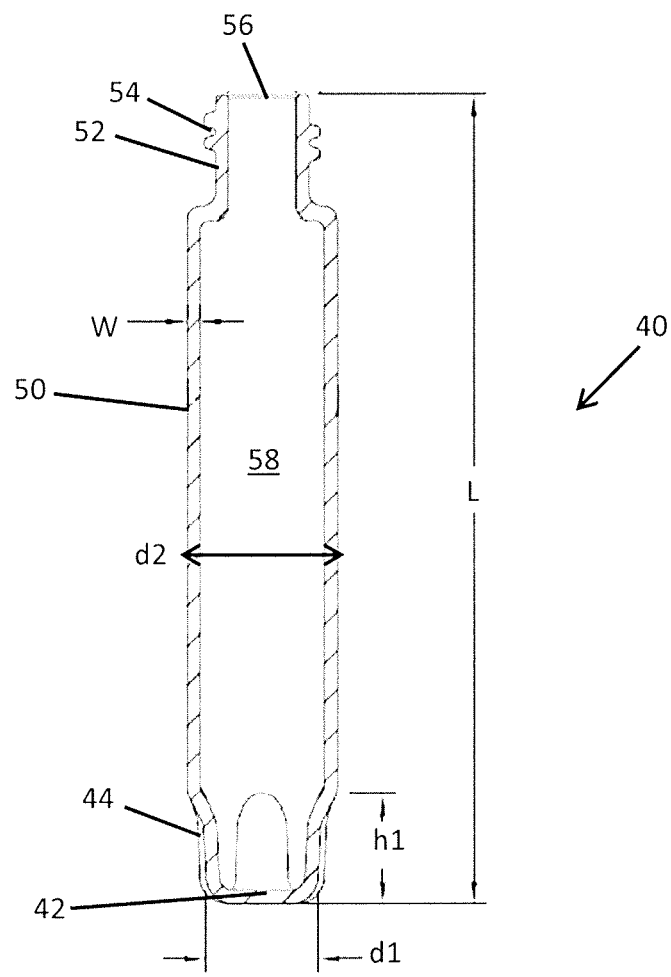
FIG. 5 shows a cross-sectional view along section 5-5 of the vial shown in FIG. 2.

The vials 40, also known as cuvettes, test tubes, ampoules, microcentrifuge tubes, microtubes, sample tubes, conical tubes, or other common terminology known in the art, are typically substantially cylindrical or tubular in shape. As depicted in FIGS. 1 and 2, the vials 40 have a longitudinal or central axis C and include a bottom wall 42, a first side wall segment 44 extending upwardly from the bottom wall 42, and a second side wall segment 50 extending from the first side wall segment 44 to an open top 56. As depicted in FIG. 5, the vials 40 have a length L extending from the bottom wall 42 to the open top 56. The second side wall segment 50, the first side wall segment 44, and the bottom wall 42 are walls of a given wall thickness W, which may be the same or different and of any suitable wall thickness W known in the art.

The second side wall segment 50, the first side wall segment 44, and the bottom wall 42 define an interior volume 58 of the vials 40. The interior volume 58 of the vials 40 may be suitable for containing a liquid or a fluid, for example. The diameter and general size of the vials 40 may define any suitable interior volume 58 known in the art, for example, suitable to accommodate tens of nanoliters to several milliliters of liquid. For a ninety-six (96) well plate assembly 10, the vials 40 may accommodate up to approximately 125 µL, for example. The size, shape, and interior volume 58 of the vials 40 may be adjusted based on the size and shape of the base plate 12 used in the well plate assembly 10. The vials 40, and particularly the second side wall segment 50, may be generally tubular in shape. In particular, the second side wall segment 50 may be substantially circular in cross section.

The first side wall segment 44 of the vials 40 includes a convoluted cross section to act as an anti-rotation feature once inserted into the base plate 12. As shown in FIG. 5, the first side wall segment 44 may have a diameter d1 which is smaller than a diameter d2 of the second side wall segment 50. For example, the diameter d1 of the first side wall segment 44 may be on the order of about 60% to 90%, 65% to 85%, or 70% to 80% of the diameter d2 of the second side wall segment 50. The first side wall segment 44 may taper toward the bottom wall 42 or may be substantially uniform in diameter d1. The first side wall segment 44 may also extend a height h1 along the entire length L of the vial 40. The height h1 is preferably less than 50%, less than 40%, less than 30%, less than 20%, or less than 10% of the length L of the vial 40. For example, the height h1 may be about 5% to about 20% or about 10% to about 15% of the entire length L of the vial 40.

Figure 6:
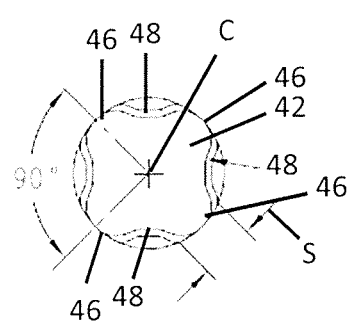
FIG. 6 shows a bottom view of the vial shown in FIG. 2.

The convoluted cross section of the first side wall segment 44 is preferably a substantially non-cylindrical, non-circular cross section. As depicted in FIG. 6, the first side wall segment 44 includes at least one spline 46. The spline 46 does not extend from an outer surface of the vial 40 (e.g., as an appendage). Instead, the spline 46 or splines 46 is or are provided in an undulating fashion to define the shape of the first side wall segment 44. The spline 46 or splines 46 may also define the interior volume 58 of the vial 40. In one embodiment, the first side wall segment 44 includes splines 46 radially extending about the central axis C separated by recesses 48 in a wave-like fashion. In other words, first side wall segment 44 includes peaks (i.e., splines 46) and valleys (i.e., recesses 48) along the outer circumference of the first side wall segment 44 for the height h1 of the vials 40.

In an exemplary embodiment, the first side wall segment 44 includes a multi-spline cross section have more than one lobe or petal. For example, the multi-spline cross section may be a bi-lobed (e.g., "butterfly" shaped or having two lobes), trefoil (e.g., "clover-leaf" shaped or having three lobes), quatrefoil (e.g., "four leaf clover" shaped or having four lobes), cinquefoil (e.g., having five lobes), sisefoil (e.g., having six lobes), or other analogous shape with at least one petal, at least two petals, at least three petals, at least four petals, at least five petals, at least six petals, or more. Any suitable number and configuration of splines 46 may be selected so long as the splines 46 operate to prevent the vial 40 from rotating once inserted in the base plate 12.

Each spline 46 may have a given width S, for example, as shown in FIG. 6. In the embodiment depicted with four splines 46 and four alternating recesses 48, the splines 46 may be provided at 90° intervals around the central axis C. The width S of each spline 46 may depend on the number and configuration of splines 46. Each spline 46 in a multi-spline cross section may have the same or varying widths S about the circumference of the first side wall segment 44. The splines 46 may also be positioned equidistant apart or may be provided with varying spacing about the circumference of the first side wall segment 44. The width S of the splines 46 may range from about 30-60% or about 45-55% of the diameter d1. In the case of four splines 46, the width S of the spline 46 may equal about the radius (i.e., half or 50% of the diameter d1) of the first side wall segment 44, for example.

The bottom wall 42 may also have a substantially non-cylindrical, non-circular cross section. In particular, the bottom wall 42 of the vial 40 may be defined in cross section by the design of the first side wall segment 44 and the portion of the first side wall segment 44 which intersects the bottom wall 42. The bottom wall 42 may also be defined by the splines 46 radially extending about the central axis C separated by recesses 48 in a wave-like fashion. In other words, the bottom wall 42 may also have a cross section including peaks (i.e., splines 46) and valleys (i.e., recesses 48) along the outer circumference of bottom wall 42. Thus, the first side wall segment 44 may define a bottom wall 42 also having the multi-spline cross section, such as bi-lobed, trefoil, quatrefoil, cinquefoil, sisefoil, or similar design, which mimics the first side wall segment 44. In an exemplary embodiment shown in FIG. 6, the first side wall segment 44 and the bottom wall 42 have a substantially quatrefoil cross section with four splines 46 and four recesses 48 separating each spline 46. The bottom wall 42 may be completely flat or the bottom wall 42 may be provided with a rim (not shown) or the like.

Figure 3:
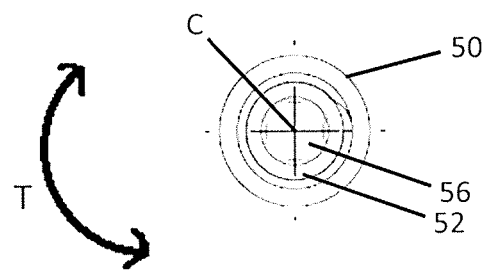
FIG. 3 shows a top view of the vial shown in FIG. 2.
Figure 4:
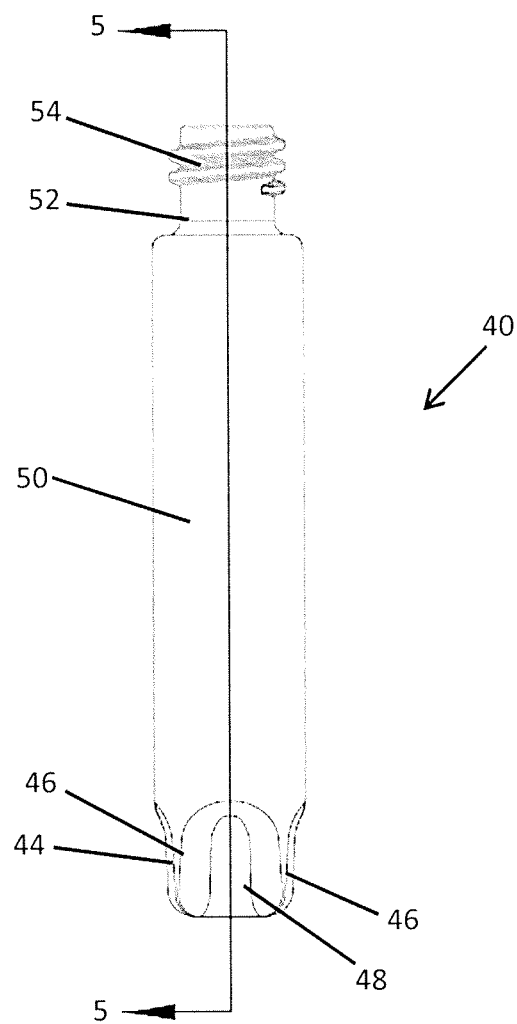
FIG. 4 provides a side view of the vial shown in FIG. 2.

As shown in FIGS. 3 and 4, the vials 40 may include a neck portion 52 to define the open top 56, which is in fluid communication with the interior volume 58 of the vial 40. The neck portion 52 may include an external thread 54 on the outer portion of the neck portion 52 designed to engage a threaded cap 70. The external thread 54 may comprise a clockwise helix or counter-clockwise helix, for example. The neck portion 52 may be of smaller diameter than the diameter d2 of the second side wall segment 50 of the vial 40. The open top 56 may include a cylindrical opening and is preferably sized such that a hypodermic needle, syringe, miniature pipette, or the like may access the interior volume 58 of the vial 40, for example, to fill or remove fluid from the vial 40.

A portion or the entirety of the vials 40 may be formed of glass or other material which is suitable for use with aqueous, acid-based, and/or solvent-based solutions. For example, the glass may be aluminosilicate glass, aluminoborosilicate glass, borosilicate glass, or the like. In particular, the glass may be a borosilicate glass, such as class A, type one borosilicate glass; type I, class B alumino-borosilicate laboratory glass, or the like. In one embodiment, the vials 40 including the bottom wall 42, the first side wall segment 44, and the second side wall segment 50 are formed of class A, type one borosilicate glass. Unlike traditional vials made of plastic, the present invention allows for the use of glass vials 40. Glass vials 40 have traditionally been unsuitable due to their low coefficient of friction and high degree of twisting or movement when a torque is applied to the vial 40. The present invention has allowed for the use of vials 40 formed exclusively of glass, however, while still providing an anti-rotation function when a torque T is applied to the vial 40. The torque T, moment, or moment of force, as evidenced in FIG. 3, is the tendency of a force to rotate an object about an axis (i.e., the central axis C). The torque T applied to the vials 40 may be encountered during capping and de-capping operations, for example.

The vials 40 may include a cap 70 including, but not limited to, threaded caps, snap caps, crimp caps, and the like. In the case of a threaded cap 70, the threaded cap 70 would have corresponding threads around its inner circumference to sealingly engage the neck portion 52 of the vial 40. The internal diameter of the threaded cap 70 may correspond to or may be slightly greater than the outer diameter of the neck portion 52. The threaded cap 70 requires a twist or rotational motion to apply the cap 70 and a reverse twist or rotational motion to remove the cap 70. Such movements may be applied by the thumb and index fingers of the user, for example. Automated equipment, such as capper and de-capper apparatus, may have a rotary gripper that screw or unscrews the caps 70 from the vials 40. Thus, the torque T is applied to the cap 70 as well as the vials 40 when the cap 70 is applied (i.e., capped) or removed (i.e., de-capped).

The vials 40 may also include a liner 72. The liner 72 may be located in the threaded cap 70, for example, above the upper-most thread. The threaded cap 70 may also have a center hole (not shown) allowing for a syringe to access liquid in the vial 40 without removing the threaded cap 70. One example of a suitable cap 70 is described in U.S. Pat. No. 7,934,614 titled "Two-Piece Seal Vial Assembly" and issued to the inventor of the present application, James G. Finneran, which is incorporated into this document in its entirety for all purposes. The cap 70 and liner 72, if present, may be made from any suitable materials known in the art. In an exemplary embodiment, the cap 70 includes a propylene threaded closure with a polytetrafluoroethylene (PTFE) and silicon liner 72.

The vials 40 may be of any suitable size as would be known to those skilled in the art. When used to retain laboratory or hospital samples involving small fluid samples, the vials 40 may have a limited volume configuration (which, in some cases, may include a separate insert (not shown). The vial 40 secures the sample within a limited volume, which facilitates handling and withdrawal of small fluid samples. If a separate insert is provided, a spring often fits between the bottom of the insert and the bottom 42 of the vial 40 to urge the insert upwardly against a closure cap and against the downward pressure of a fluid-withdrawing instrument. The insert is typically a conical-bottomed inner container, from which fluid sample is withdrawn by a hypodermic needle, syringe, or miniature pipette. Upward biasing of the insert and the conical shape of the internal volume of the insert permit the fine needle or pipette to be pressed into the very bottom of the insert, without damage, to assure complete withdrawal of fluid sample. U.S. Pat. No. 5,108,386 titled "Spring and Container with Spring Biased Inner Container Insert" and issued to the inventor of the present application, James G. Finneran, which is incorporated into this document in its entirety for all purposes, discloses an improvement in such containers by which complete withdrawal of fluid sample is better assured. The limited volume section may have a conical bottom, from which small fluid sample can be withdrawn by a hypodermic needle, syringe, or miniature pipette.

Base Plate

Figure 8:
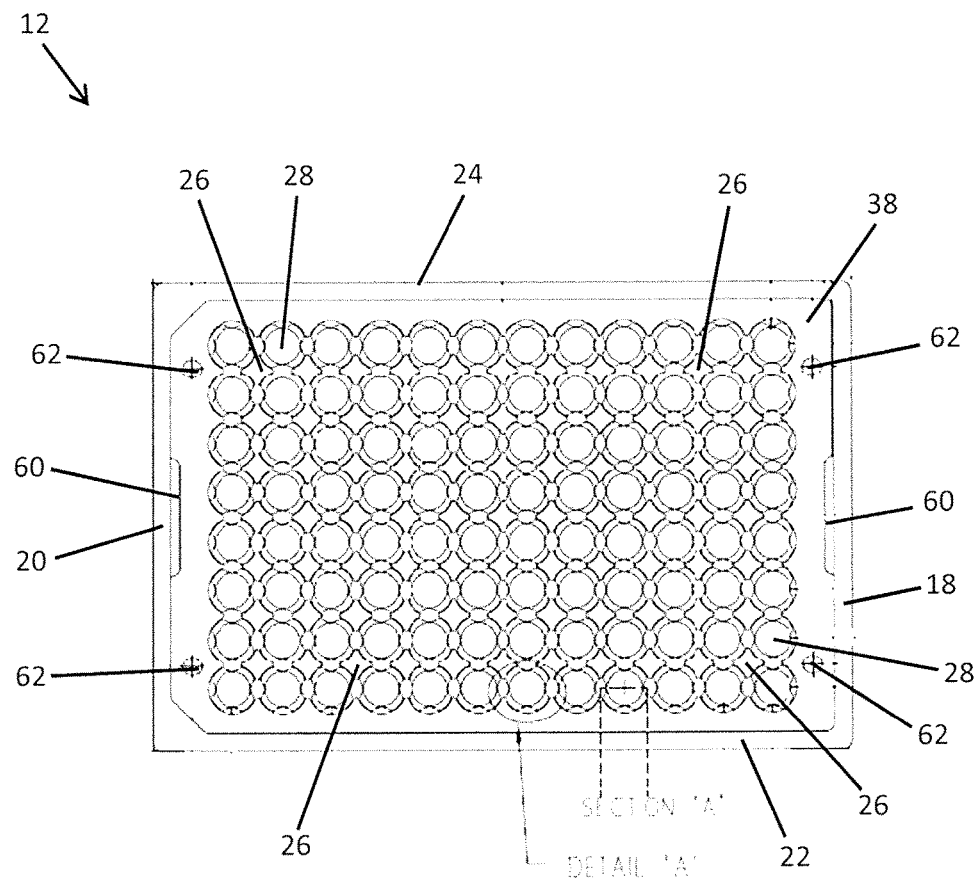
FIG. 8 provides a top view of the base plate shown in FIG. 1.

As depicted in FIG. 1, the base plate 12 also known as a well plate, microplate, microtitre plate, vial plate, tray, vial-holding device, or other common terminology known in the art, includes a bottom 14 and a perimeter 16 having a top surface 38. FIG. 8 depicts a top view of the base plate 12. The perimeter 16 may be a solid perimeter defining the outer edges of the base plate 12. For example, the perimeter 16 may be defined by opposing edges including a first edge 18, a second edge 20, a front edge 22, and a back edge 24. Although a rectangular cross section is shown, the base plate 12 may have any suitable cross section, such as a circular, oval, square, or the like.

Figure 7:
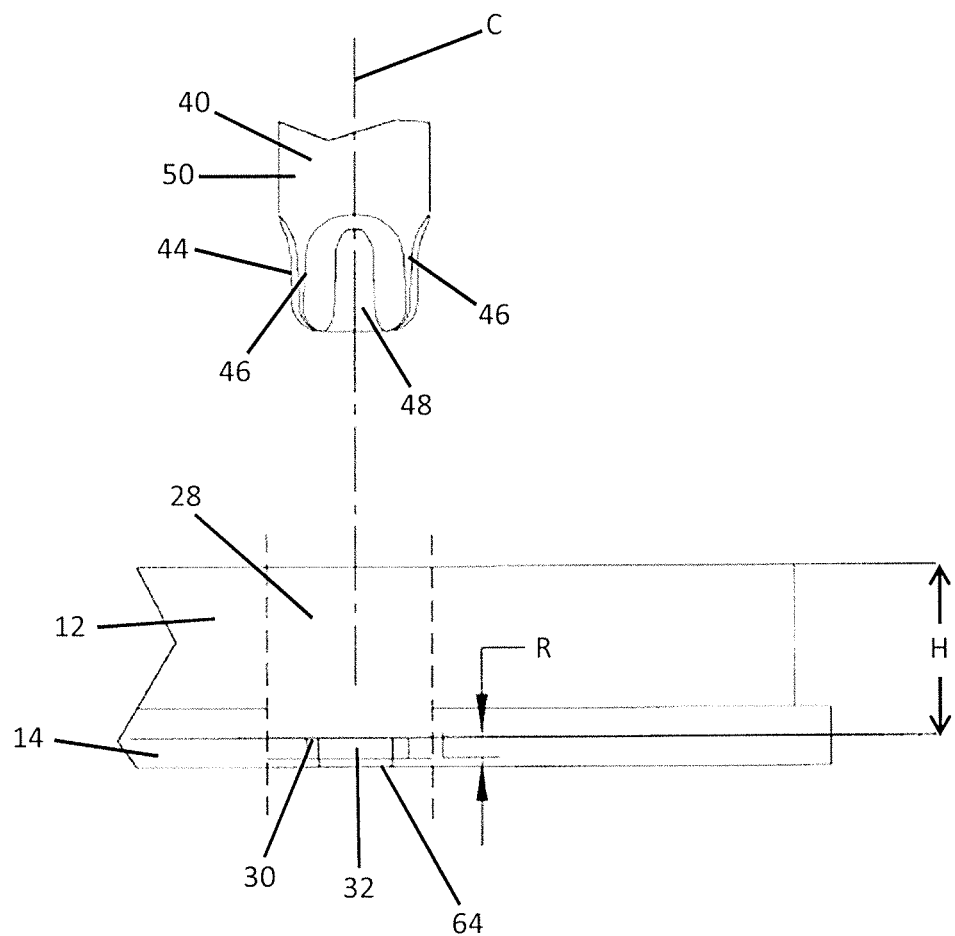
FIG. 7 shows a close-up side view of the base of the vial and the corresponding compartment in the base plate.

The base plate 12 includes a plurality of protrusions 26 extending from the bottom 14 of the base plate 12 to define a plurality of compartments 28. FIG. 7 depicts one compartment 28 in the base plate 12. The protrusions 26 may extend from the bottom 14 to a height H, for example, substantially even with the top surface 38 of the perimeter 16 of the base plate 12. The protrusions 26 are preferably unconnected to and independent from one another. The protrusions 26 may be provided in an array of rows and columns. Typical arrays may include a suitable number of protrusions 26 to provide, for example, 6, 12, 24, 48, 96, 384 or 1536 compartments 28. For example, rows and columns of four by six (4×6) for twenty-four (24) compartments 28 or eight by twelve (8×12) for ninety-six (96) compartments 28 may be provided. The protrusions 26 are spaced apart and independent from each other to form the plurality of compartments 28, which are sized and configured for releasably holding the vials 40. In other words, the compartments 28 are able to securely hold each respective vial 40 in an upright and substantially vertical orientation. These compartments 28 allow the base plate 12 to hold one or more individual vials 40 without the need for a series of vials 40 to be attached to each other.

Figure 10:
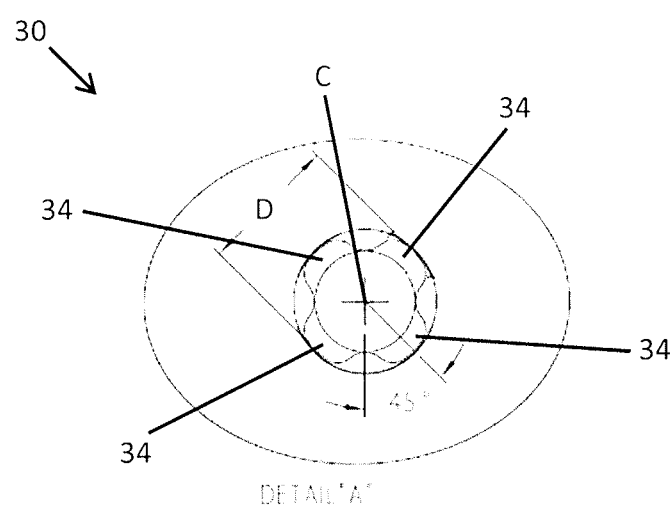
FIG. 10 shows a close-up top view including Detail A of one compartment in the base plate shown in FIG. 8.
Figure 11:
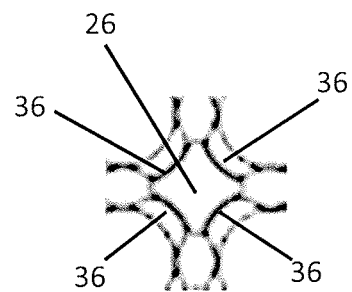
FIG. 11 shows a close-up top view of one diamond-shaped protrusion from the base plate.

The protrusions 26 may be shaped so that they conform around the outer surface of the vials 40 when the vials 40 are inserted into the compartments 28. The protrusions 26 may be of any suitable shape, for example, triangular, rectangular, or the like. In an exemplary embodiment, the protrusions 26 are substantially diamond-shaped. As best seen in FIG. 11, each side of the diamond-shaped protrusions 26 may have a concave side 36. Thus, the compartments 28 may have scalloped or concaved sides 36 where the compartments 28 contact the vials 40 in order to accommodate round vials 40. In other words, the protrusions 26 are designed to accommodate the second side wall segment 50, which is substantially tubular in shape. The protrusions 26 may be designed to form compartments 28 having a diameter D (see FIG. 10) which is equal to or slightly less than the diameter d2 of the second side wall segment 50.

In an exemplary embodiment, the protrusions 26 are in the shape of a superellipse. For example, the superellipse may be defined in the Cartesian coordinate system as the set of all points (x, y) with:

$$\left|\frac{x}{a}\right|^n + \left|\frac{y}{b}\right|^n = 1$$

where n, a, and b are positive numbers. The parameters a and b are the semi-diameters of the curve and n is preferably between 0 and 1. In particular, the superellipse may be in the form of a hypoellipse. The semi-diameters of the curve may be the same and may approximate the diameter d2 of the second side wall segment 50. FIG. 11 depicts an exemplary shape for the superellipse.

Figure 9:
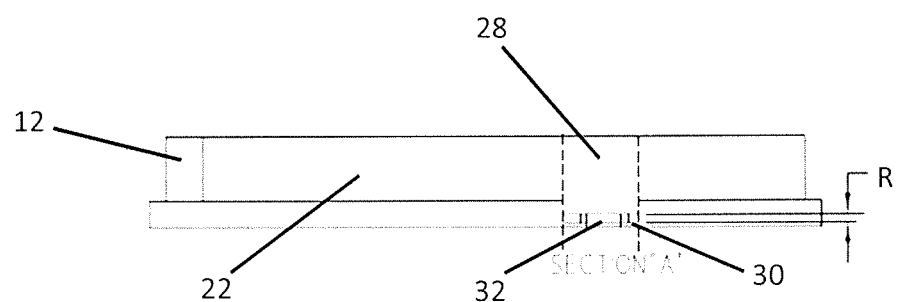
FIG. 9 shows a front view of the base plate including one compartment labeled Section A shown in FIG. 8.

Each of the compartments 28, defined by the protrusions 26, includes a convoluted anti-rotation feature 30 designed to engage the bottom wall 42 and at least a portion of the first side wall segment 44 of the vials 40. The convoluted anti-rotation feature 30 is recessed into the bottom 14 of the base plate 12. In particular, as depicted in FIGS. 9 and 10, the convoluted anti-rotation feature 30 includes a recess 32 having a substantially non-cylindrical, non-circular cross section. As shown in FIGS. 7 and 9, the recess 32 of the anti-rotation feature 30 may be provided at a depth R. The depth R of the recess 32 may be equal to or less than the height h1 of the first side wall segment 44. In an exemplary embodiment, the depth R of the recess 32 is less than the height h1 of the first side wall segment 44 of the vial 40. In particular, the depth R of the recess 32 may be about 5 to about 75%, about 10 to about 50%, about 20 to about 40%, about 25 to about 35%, or about 30% of the height h1 of the first side wall segment 44. This configuration accommodates different vials 40 which may have different heights h1 while still providing sufficient fit of the bottom wall 42 and a portion of the first side wall segment 44 into the recess 32.

In one embodiment, the recess 32 includes at least one lobe 34. The lobe 34 or lobes 34 is or are provided in an undulating fashion to define the shape of the recess 32. The lobes 34 may be radially extending about the central axis C separated by projections in a wave-like fashion. In other words, the recess 32 includes peaks (i.e., lobes 34) and valleys (i.e., material of the bottom 14 of the base plate 12) to define a shape which is the mirror image of the bottom wall 42 and the first side wall segment 44 of the vials 40.

In an exemplary embodiment, the recess 32 includes a multi-lobe cross section having more than one lobe 34. For example, the multi-lobe cross section may be a bi-lobed (e.g., "butterfly" shaped), trefoil (e.g., "clover-leaf" shaped), quatrefoil (e.g., "four leaf clover" shaped), cinquefoil, sisefoil, or other analogous shape with at least one petal, at least two petals, at least three petals, at least four petals, at least five petals, at least six petals, or more. Any suitable number and configuration of lobes 34 may be selected so long as the lobes 34 operate to prevent the vials 40 from rotating and substantially align with or match the number and configuration of splines 46 on the bottom wall 42 and the first side wall segment 44 of the vials 40.

As seen in FIG. 7, the bottom 14 of the base plate 12 may also include a plurality of openings 64. These openings 64 may be centrally aligned with the plurality of compartments 28 or may be positioned at any suitable location in the bottom 14 of the base plate 12. These openings 64 may allow for any accumulated liquids to empty from the base plate 12. The base plate 12 may be formed in a unitary one-piece construction, for example. The base plate 12 may also be formed from any suitable material, such as a polymer material or a metallic material. The base plate 12 may be formed from a polymer material, such as polypropylene, polyvinylchloride, or polystyrene, by injection molding, blow molding, or another form of plastic molding known in the art. In other embodiments, the base plate 12 comprises a metallic material, such as aluminum, zinc, magnesium, copper, or their alloys. In an exemplary embodiment, the base plate 12 is formed of aluminum or an aluminum alloy.

Figure 12:
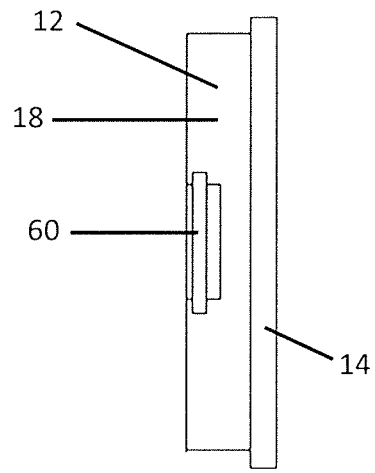
FIG. 12 shows a side view of the base plate shown in FIG. 1.

The base plate 12 may further include one or more grooves 60, for example, in order to engage a cover (not shown). As depicted in FIG. 8 and FIG. 12, the base plate 12 may include grooves 60 on the first edge 18, and similar grooves 60 may be provided on the second edge 20. The base plate 12 may also include one or more holes 62 extending from the top surface 38 to a given depth, for example, in order to allow for stacking of the base plates 12 or to engage a cover (not shown).

Well Plate Assembly

The well plate assembly 10 includes the base plate 12 having the convoluted anti-rotation feature 30 recessed into the bottom 14 of the base plate 12 and the vials 40 having the bottom wall 42 and first side wall segment 44 with a matching and corresponding convoluted cross section. The vials 40 may be placed into the compartments 28 defined by the plurality of protrusions 26 and the bottom wall 42 and at least a portion of the first side wall segment 44 fit within the recess 32 in the bottom 14 of the base plate 12. FIG. 7 depicts a single compartment 28 and single vial 40, which may be placed into and housed within the compartment 28.

The compartments 28 are adapted to releasably hold the tubular vials 40, such that the vials 40 may be inserted and removed from the base plate 12 in a linear fashion. The recess 32 in the base plate 12 is adapted to prevent rotation of the vials 40 when the torque T is applied to the vials 40, for example, during automated capping or de-capping operations. In other words, the bottom wall 42 and the first side wall segment 44 of the vial 40 preferably correspond to and match the convoluted anti-rotation feature 30 recessed into the bottom 14 of the base plate 12. When the bottom wall 42 and at least a portion of the first side wall segment 44 of the vial 40 are inserted into the anti-rotation feature 30, a transition fit or an interference fit is thereby created preventing rotational movement of the vials 40 depending on the clearance between the first side wall segment 44 and the recessed anti-rotation feature 30.

The vials 40 preferably include a multi-spline cross section with more than one spline, for example, such as bi-lobed, trefoil, quatrefoil, cinquefoil, sisefoil, or the like, and the convoluted anti-rotation feature 30 includes the same or substantially the same cross section including bi-lobed, trefoil, quatrefoil, cinquefoil, sisefoil, or the like. In an exemplary embodiment, the bottom wall 42 and the first side wall segment 44 of the vials 40 as well as the recessed convoluted anti-rotation feature 30 in the base plate 12 have a substantially quatrefoil cross section with four lobes.

The present invention provides for an improved well plate assembly 10 that allows for use of glass vials 40 suitable for use with aqueous, acid-based, and/or solvent-based solutions. The glass vials 40 and the base plate 12 are designed to mate together and prevent rotation of the vials 40. In particular, rotation of the vials 40 may be minimized or eliminated when the torque T is applied to the vials 40, for example, during capping or de-capping of the vials 40.

The well plate assembly 10 of the present invention may be used with analytical chemistry assays and vials 40 used in assays related to drug metabolism, screening in combinatorial chemistry, high-throughput screening, sorbent assays, and the like. The base plate 12 and the vials 40 are designed to be compatible with automated capping and de-capping instruments, autosamplers, and the like.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A well plate assembly comprising:
    a base plate having a bottom, a perimeter having opposing edges, and a plurality of protrusions extending from the bottom spaced apart from each other to form a plurality of compartments sized and configured for releasably holding vials, wherein each of the compartments includes a convoluted anti-rotation feature recessed into the bottom, the convoluted anti-rotation feature having at least one lobe; and
    a plurality of glass vials each having a central axis, a bottom wall, a first side wall segment extending upwardly from the bottom wall, and a second side wall segment extending from the first side wall segment to an open top, wherein the first side wall segment includes at least one spline radially extending about the central axis, the at least one spline designed to mate with the at least one lobe of the convoluted anti-rotation feature to fix the glass vials in position and prevent rotation of the glass vials when a torque is applied, wherein the first side wall segment and the bottom wall are a mirror image of the convoluted anti-rotation feature recessed into the bottom of the base plate.

2. The well plate assembly of claim 1, wherein the convoluted anti-rotation feature has a multi-lobed cross section selected from the group consisting of bi-lobed, trefoil, quatrefoil, cinquefoil, and sisefoil.

3. The well plate assembly of claim 2, wherein the bottom wall and the first side wall segment of the glass vials include a multi-spline cross section selected from the group consisting of bi-lobed, trefoil, quatrefoil, cinquefoil, and sisefoil.

4. The well plate assembly of claim 1, wherein the bottom wall of the glass vials has a substantially quatrefoil cross section.

5. The well plate assembly of claim 1, wherein the first side wall segment of the glass vials has a substantially quatrefoil cross section.

6. The well plate assembly of claim 1, wherein the second side wall segment of the glass vials has a substantially circular cross section.

7. The well plate assembly of claim 1, wherein the vials are formed of class A, type one borosilicate glass.

8. The well plate assembly of claim 1, wherein the glass vials further comprise an externally threaded neck.

9. The well plate assembly of claim 1, wherein each of the protrusions is substantially diamond-shaped.

10. The well plate assembly of claim 1, wherein the protrusions are unconnected to one another and each protrusion is a superellipse.

11. The well plate assembly of claim 1, wherein the bottom of the base plate includes a plurality of openings centrally aligned with the plurality of compartments.

12. The well plate assembly of claim 1, wherein the base plate is formed in a unitary one-piece construction.

13. The well plate assembly of claim 1, wherein the glass vials further comprise a cap selected from the group consisting of crimp caps, snap caps, and threaded caps.

14. The well plate assembly of claim 1, wherein the glass vials further comprise a propylene threaded closure with a polytetrafluoroethylene and silicon liner.

15. The well plate assembly of claim 1, wherein the torque is applied to the glass vials during an automated capping or de-capping operation.

16. A well plate assembly comprising:
    a base plate having a bottom, a perimeter having opposing edges, and an array of individual, substantially diamond-shaped protrusions extending from the bottom spaced apart from each other to form a plurality of compartments sized and configured for releasably holding tubular vials, wherein each of the compartments includes a convoluted anti-rotation feature recessed into the bottom, the convoluted anti-rotation feature defining a multi-lobed cross section having a plurality of lobes; and
    a plurality of glass vials each having a central axis, a bottom wall, a first side wall segment extending upwardly from the bottom wall, and a second side wall segment extending from the first side wall segment to an externally threaded neck portion having an open top, wherein the first side wall segment includes splines radially extending about the central axis separated by recesses and defining the bottom wall to have a multi-spline cross section, the bottom wall and the splines designed to mate with the respective lobes of the recessed anti-rotation feature to fix the vials in position and prevent rotation of the vial when a torque is applied, wherein the first side wall segment and the bottom wall are a mirror image of the convoluted anti-rotation feature recessed into the bottom of the base plate.

* * * * *